United States Patent
Tortorella

(10) Patent No.: US 6,635,430 B1
(45) Date of Patent: Oct. 21, 2003

(54) FILTRATE PLATE DEVICE AND REVERSIBLE-WELL PLATE DEVICE

(75) Inventor: Micky D. Tortorella, Newark, DE (US)

(73) Assignee: DuPont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 09/540,030

(22) Filed: Mar. 31, 2000

Related U.S. Application Data

(60) Provisional application No. 60/127,624, filed on Apr. 1, 1999, and provisional application No. 60/145,527, filed on Jul. 16, 1999.

(51) Int. Cl.$^7$ .............................................. G01N 33/53
(52) U.S. Cl. ........................... 435/7.1; 422/58; 422/99; 422/101; 422/102; 422/104; 435/288.3; 435/288.4; 436/809
(58) Field of Search ............................. 422/58, 99, 101, 422/102, 104; 435/288.3, 288.4, 7.1; 436/809

(56) References Cited

U.S. PATENT DOCUMENTS

| | | | |
|---|---|---|---|
| 4,154,795 A | * 5/1979 | Thorne | 422/99 |
| 4,427,415 A | * 1/1984 | Cleveland | 436/57 |
| 4,493,815 A | * 1/1985 | Fernwood et al. | 422/101 |
| 4,735,778 A | * 4/1988 | Maruyama et al. | 422/102 |
| 4,770,856 A | * 9/1988 | Uthemann et al. | 422/104 |
| 4,777,021 A | * 10/1988 | Wertz et al. | 422/101 |
| 4,797,259 A | * 1/1989 | Matkovich et al. | 422/101 |
| 4,895,706 A | * 1/1990 | Root et al. | 422/102 |
| 4,948,442 A | * 8/1990 | Manns | 436/809 |
| 4,948,564 A | * 8/1990 | Root et al. | 422/102 |
| 5,084,246 A | * 1/1992 | Lymann et al. | 422/101 |
| 5,200,474 A | 4/1993 | Chen et al. | 525/426 |
| 5,227,137 A | * 7/1993 | Monti et al. | 422/101 |
| 5,853,894 A | * 12/1998 | Brown | 427/2.1 |
| 6,309,605 B1 | 10/2001 | Zermani | 422/101 |

* cited by examiner

Primary Examiner—Christopher L. Chin
(74) Attorney, Agent, or Firm—Nields & Lemack

(57) ABSTRACT

This invention is directed to filtrate-holder and reversible-well collection plates composed of polypropylene and Teflon®, and to their use, in connection with compatible filter units, in high-throughput screening assays for assessing the binding of small molecules to proteins.

9 Claims, 13 Drawing Sheets

The Tortorella filtrate holder. The holder contains a novel micro-array format which allows it to hold 96 Microcon filter units. The holder contains 96 through holes where the base of filter unit passes through and protrudes into the Tortorella filtrate collection plate.

The Microcon-10 filter unit and collection tube. The Microcon-10 filter unit consists of a reservoir which holds up to 500 μl of liquid, the YM membrane and a base which directs the filtrate into the microfuge collection tube during centrifugation.

Correlation between equilibrium dialysis and Microcon-10 centrifugation. The amount of serum binding of 50 small molecules were calculated using standard equilibrium dialysis and Microcon-10 centrifugation. The binding values generated in the two assays were compared and a correlation curve plotted. The $R^2$ value is 0.98.

The Tortorella filtrate holder. The holder contains a novel micro-array format which allows it to hold 96 Microcon filter units. The holder contains 96 through holes where the base of filter unit passes through and protrudes into the Tortorella filtrate collection plate.

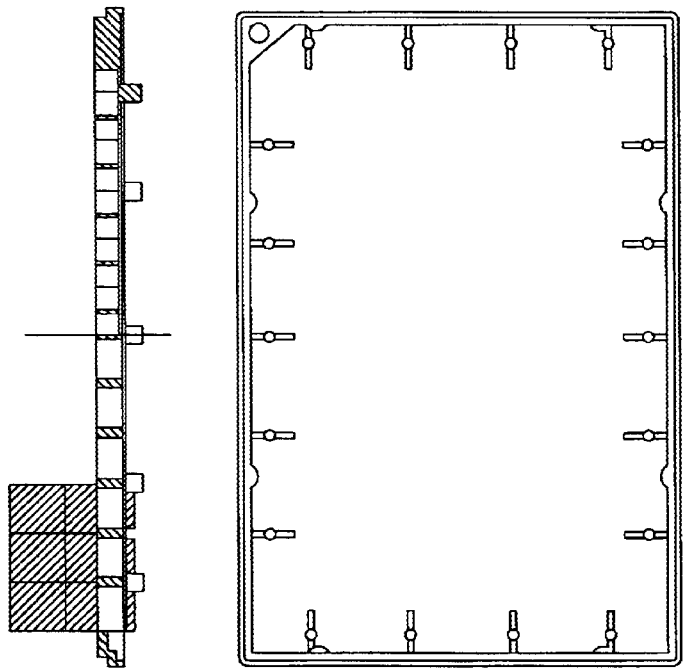

The Tortorella filtrate holder. The diagram is a side and bottom view of the holder. The side view illustrates the penetration of the Microcon filter units into the through holes of the holder. The ridge of the filter unit lies on top of the well and the base protrudes several millimeters. The bottom of the holder contains several protruding pegs which clamp into the Tortorella filtrate collection plate. This allows the holder to fit tightly on top of the collection plate during centrifugation.

FIG. 5

The Tortorella filtrate holder. The diagram illustrates the assembly of the Tortorella filtrate holder and collection plate. The holder containing 96 Microcon units is placed on top of the collection plate. The base of the filter units protrude into the wells and the pegs on the bottom of the holder seal the two parts.

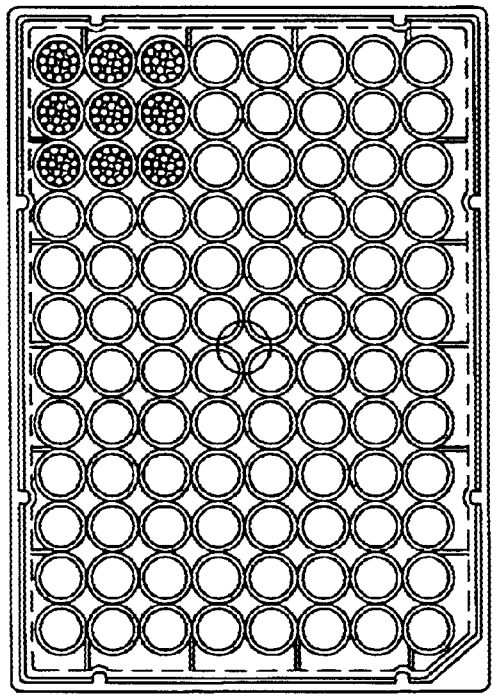

The Tortorella filtrate collection plate. The collection plate contains a novel micro-array format which allows it to hold 96 Microcon filter units. The plate is compatible with the Tortorella filtrate holder. The plate contains flat bottom wells with the exterior dimensions of a standard 96-well plate. The plate contains V-grooves which make the plate compatible with robotic arms.

FIG. 7

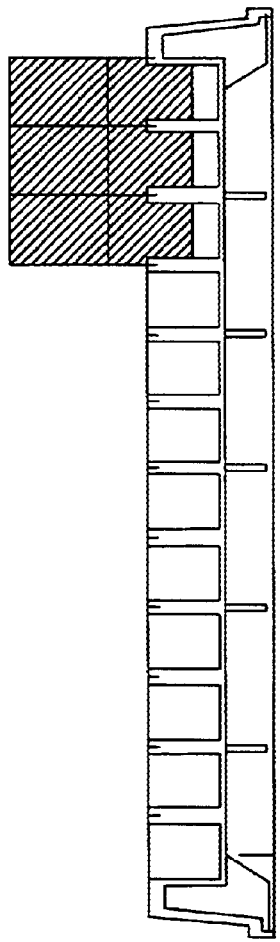

FIG. 8

The Tortorella filtrate collection plate. The diagram is a side view of the Tortorella filtrate collection plate. The plate is designed to hold 96 Microcon filter units. The filter unit can be directly inserted into the well. The ridge of the filter unit lies on top of the outside of the well, allowing just the base of the filter unit to protrude into the wells. This feature prevents well to well spill-over during centrifugation of samples.

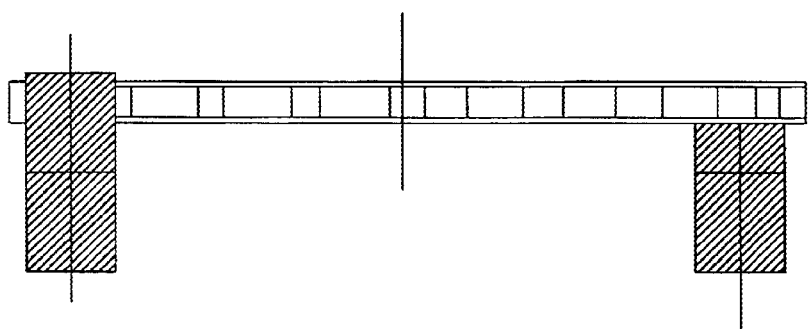

FIG. 9

The Tortorella reversible well holder. The holder contains a novel micro-array format which allows it to hold 96 Microcon filter units. The holder contains 96 through holes where the base of filter units pass through and protrude into the wells of the Tortorella-reversible well collection plate for the retrieval of the filtrate. The holder also aligns into the wells of the Tortorella-reversible well collection plate for the retrieval of the filtrate. The holder also aligns the open end of the Microcon reservoirs which can also fit into the wells of the reversible well collection plate. This feature makes the 96-well invert spin possible.

The Tortorella reversible well holder. The diagram is a side view of the alignment of Tortorella retentate holder and collection plate. The diagram illustrates that the micro-array format between the holder and collection plate are in alignment.

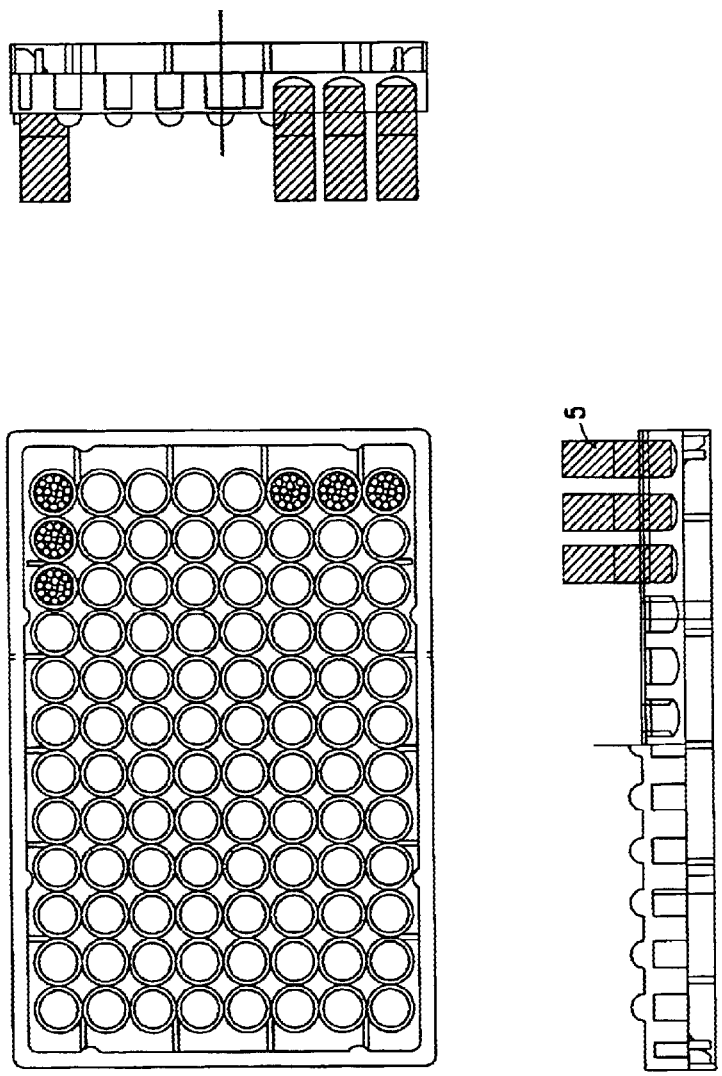

FIG. 11

The Tortorella reversible well collection plate. The collection plate contains a novel micro-array format which allows it to hold 96 Microcon filter units. The plate was designed to allow the wells to fit into either end of the filter units. The reversible well collection plate can be used for the collection of both the filtrate and retentate. The plate is compatible with the Tortorella reversible well holder. The plate contains U-bottom wells with the exterior dimensions of a standard 96-well plate. The plate contains V-grooves which make it compatible with robotic arms.

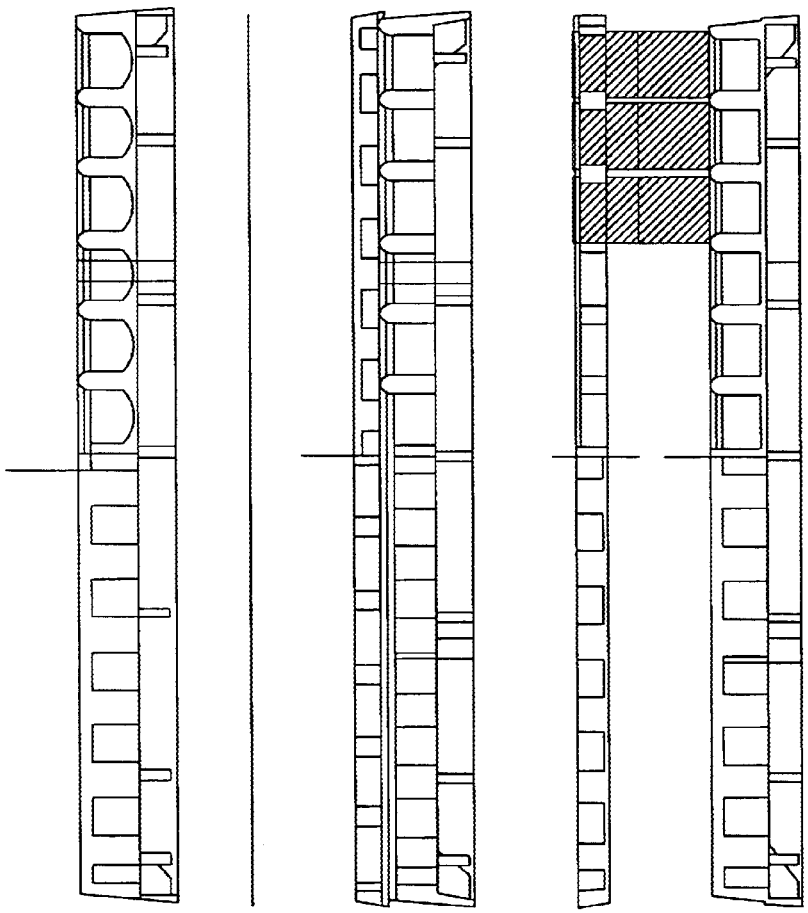

FIG. 12

The Tortorella reversible well collection plate. The side view of the reversible well collection plate illustrates how both sides of the Microcon filter units contained in the holder can fit into the wells. The raised bumps formated on the collection plate allow the open end of the Microcon reservoirs to fit tightly into the wells. This unique feature allows for the collection of both the filtrate and retentate in a single experiment without well to well spill over.

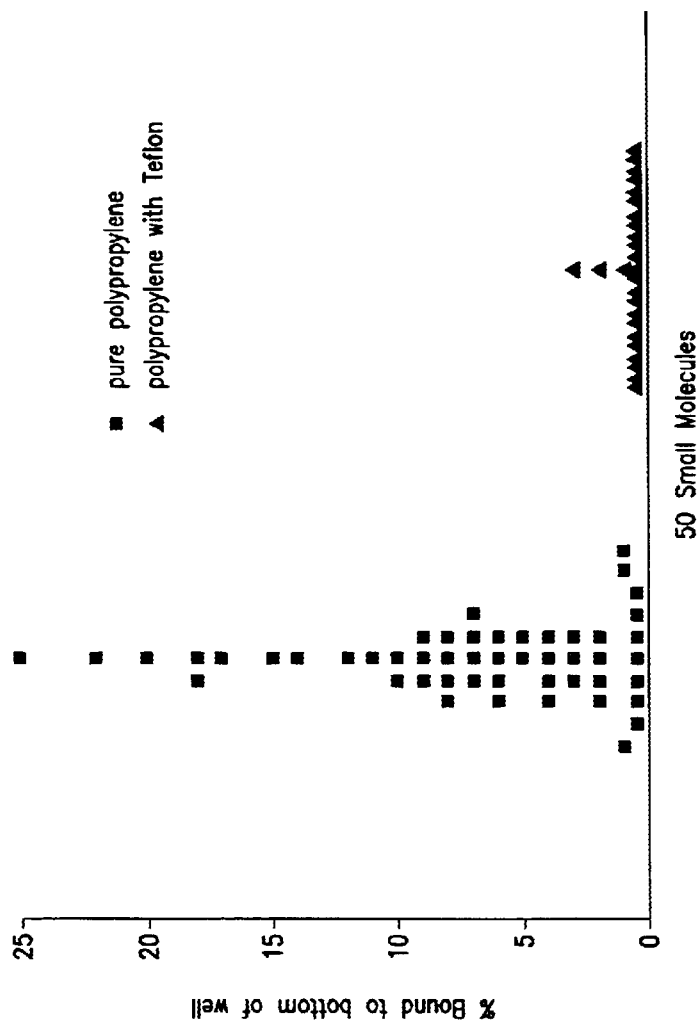

FIG. 13

Binding of small molecules to polypropylene and polypropylene with Teflon. The binding of 50 small molecules to polypropylene and polypropylene with 2.5 % Teflon was determined by incubating each molecule at a range of concentrations, 1–1000 nM, with each of two plastic plates. The drug was allowed to incubate in the well in a volume of 500 μl water for 30 minutes at 37°C. Following the incubation the samples were collected and the drug concentrations were calculated. The decrease in concentration was used to calculate the levels of binding to plastic.

FILTRATE PLATE DEVICE AND REVERSIBLE-WELL PLATE DEVICE

This application claims the benefit of the filing dates of U.S. Provisional Application Ser. Nos. 60/127,624 filed Apr. 1, 1999 and 60/145,527 filed Jul. 16, 1999.

FIELD OF THE INVENTION

This invention relates to novel plate devices for use in high-throughput screening assays.

BACKGROUND OF THE INVENTION

The binding of small molecules and peptides to protein is a very important parameter to measure in the pharmaceutical industry. As pharmaceutical companies strive to design novel small molecules and peptides to treat various ailments ranging from life threatening diseases including cancer, AIDS, and heart disease to cosmetic complaints such as ACNE, age spots and wrinkles, successful administration of these drugs through the circulatory system is critical. Many drugs that have been shown to be very active in vitro assays have failed to show efficacy in animal models and in people because of the high plasma protein binding exhibited by these compounds. When a molecule is highly bound to proteins in the blood the amount of drug available to diffuse into the target tissue is significantly reduced and the efficacy of the drug will inevitably be poor.

Whether a small molecule binds to plasma proteins or not usually depends on the size of the molecule, the amino acid composition and the tertiary structure of the molecule. When a small molecule binds to plasma proteins the interaction usually is a result of strong ionic and hydrophobic interactions. Because blood contains several hundred proteins there is a high probability that any small molecule will exhibit some level of binding. Determining the level of binding therefore is critical and will directly correlate with efficacy of the molecule. Predicting whether a molecule is going to show high or low protein binding based on molecular structure has proven to be very difficult. The only sure way to determine whether or not a molecule will exhibit high or low protein binding is to test the molecule directly in a protein-binding assay.

The most common method used to measure the level of protein binding exhibited by compounds is equilibrium dialysis assays. In such assays, a set concentration of drug (usually 1·M) is added to a set volume of human plasma (usually 3 ml). The mixture is added to dialysis tubing with a molecular weight cut-off of 30 kDa. The mixture is allowed to incubate in a large volume of water (usually 4 liter) for 24 hours at 37° C. Following the incubation the sample is collected and the concentration of drug is calculated. If the compound is completely unbound to protein, the concentration following dialysis would be 0, if 50% bound the concentration would be 0.5 uM, etc. Although equilibrium dialysis has been shown to be accurate and consistent, it is very time consuming and the number of drugs a researcher can test in one assay is dependent on how many 4-liter beakers he/she can set up. Thus, the need for a fast, high-throughput assay is needed in the pharmaceutical industry.

SUMMARY OF THE INVENTION

This invention is directed to a filtrate-holder plate comprising polypropylene and Teflon®, most preferably about 2.5% Teflon® and about 97.5% polypropylene. Said plate contains 96 wells each of which is capable of securely holding a Microcon-3, 10, 30 or 100® filter unit (see FIGS. 4, 5, 7 and 8). Said filter unit (see FIG. 1) contains a reservoir and a filter membrane, contained within the filtrate plate. The filter unit also contains a base, which passes through an opening in each of the filtrate plates 96 wells and into a reversible-well collection plate (see FIGS. 9, 10, 11 and 12). Said "reversible-well collection plate", also comprises polypropylene and Teflon® (most preferably, again, at about 2.5% Teflon® and about 97.5% polypropylene) and also contains 96 wells. The reversible-well plate is designed such that its wells can accommodate either end of the Micron-3, 10, 30 or 100® filter unit.

The filtrate-holder and reversible-well plates, along with the filter units contained therein, are securely fastened together and used in high-throughput screening assays for the binding of small molecules and peptides to proteins. The design of the plates, and their composition, allows for several advantages in the conducting of such screens, as is described herein.

BRIEF DESCRIPTION OF THE DRAWINGS

FIG. 5—Filtrate Holder. The diagram is a side and bottom view of the holder. The side view illustrates the penetration of the Microcon filter units into the through holes of the holder. The ridge of the filter unit lies on top of the well and the base protrudes several millimeters. The bottom of the holder contains several protruding pegs which clamp into the filtrate collection plate. This allows the holder to fit tightly on top of the collection plate during centrifugation.

FIG. 7—Filtrate Holder. Top view of the collection plate containing a novel micro-array format which allows it to hold 96 Microcon filter units. The plate is compatible with the filtrate holder. The plate contains flat bottom wells with the exterior dimensions of a standard 96-well plate. The plate contains V-grooves which make the plate compatible with robotic arms.

FIG. 8—The diagram is a side view of the filtrate-holder plate. The plate is designed to hold 96 Microcon filter units. The filter unit can be directly inserted into the well. The ridge of the filter unit lies on top of the outside of the well, allowing just the base of the filter unit to protrude into the wells. This feature prevents well-to-well spill-over during centrifugation of samples.

FIG. 9—Reversible-Well Collection Plate. The plate contains a novel micro-array format which allows it to hold 96 Microcon filter units. The holder contains 96 through holes where the base of filter units pass through and protrude into the wells of the -reversible-well collection plate for the retrieval of the filtrate. The holder also aligns the open end of the Microcon reservoirs which can also fit into the wells of the reversible well-collection plate. This feature makes the 96-well invert spin possible.

FIG. 11—Reversible-Well Collection Plate. The collection plate contains a novel micro-array format which allows it to hold 96 Microcon filter units. The plate was designed to allow the wells to fit into either end of the filter units. The reversible-well collection plate can be used for the collection of both the filtrate and retentate. The plate is compatible with the reversible-well holder. The plate contains U-bottom wells with the exterior dimensions of a standard 96-well plate. The plate contains V-grooves which make it compatible with robotic arms.

FIG. 12—Reversible-Well Collection Plate. The side view of the reversible-well collection plate illustrates how both sides of the Microcon filter units contained in the holder can fit into the wells. The raised bumps formed on the collection plate allow the open end of the Microcon reservoirs to fit tightly into the wells. This unique feature allows for the collection of both the filtrate and retentate in a single experiment without well to well spill over.

FIG. 13—Binding of Small Molecules to Polypropylene and Polypropylene with Teflon®. The binding of 50 small molecules to polypropylene and polypropylene with 2.5% Teflon was determined by incubating each molecule at a range of concentrations, 1–1000 nM, with each of two plastic plates. The drug was allowed to incubate in the well in a volume of 500 ul water for 30 minutes at 37° C. Following the incubation the samples were collected and the drug concentrations were calculated. The decrease in concentration was used to calculate the levels of binding to plastic.

DETAILED DESCRIPTION OF THE INVENTION

Figure 1:
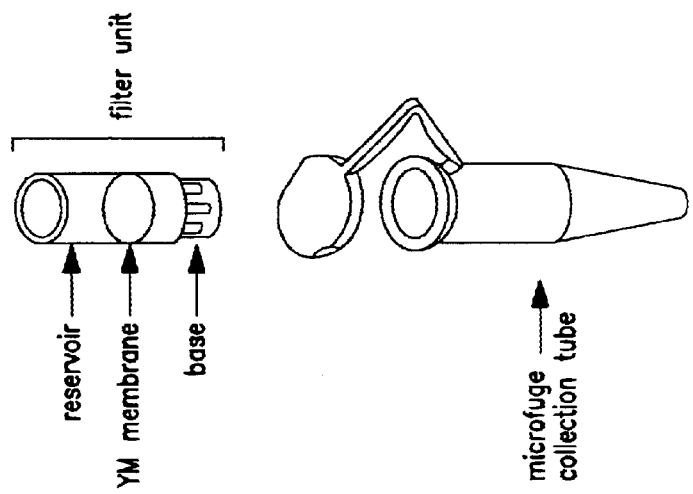
FIG. 1—Microcon-10 filter unit and collection tube. The Microcon-10 filter unit consists of a reservoir which holds up to 500·1 of liquid, the YM membrane and a base which directs the filtrate into the microfuge-collection tube during centrifugation.

This invention provides a filtrate-holder plate (see FIGS. 4, 5, 7 and 8) comprising polypropylene and Teflon® and containing 96 wells, wherein: each of said wells is capable of securely containing a Microcon-3, 10, 30 or 100® filter unit; said wells contain an opening on their bottom surface sufficient in size to allow the base of said filter unit, but not the reservoir or filter membrane of said filter unit, to pass through the bottom surface and into a filtrate collection plate; said wells have a circular circumference; said wells are arranged in 8 rows of twelve wells each in the plate; the center of each well is aligned vertically with the wells in the rows above and below said well and the center of each well is aligned horizontally with the center of the wells in columns to the left and right of said well; and wherein: the exterior bottom surface of said filtrate-holder plate contains a plurality of pegs protruding therefrom sufficient in number and size to connect said plate to a reversible-well collection plate (said "reversible-well collection plate" is the reversible collection plate described and claimed herein); the side and bottom surfaces of said filtrate-holder plate contain a plurality of V-shaped grooves sufficient in number and size to allow the plate by a standard automated device (i.e., a device typically used in screening laboratories for the expedient processing of a large number of plates); the external dimensions of said filtrate-holder plate are about the same as the external dimensions of a standard 96-well plate used for high-throughput screening assays. Preferably, said filtrate-holder plate is composed of from about 1–10% Teflon® and from about 80–99% polypropylene, most preferably, of about 2.5% Teflon® and about 97.5% polypropylene. This combination of Teflon® inhibits the binding of molecules to the surface of the wells of the plates, and thus makes for more efficient and reliable assays. Said filtrate-holder plate is substantially as described in FIGS. 4, 5, 7 and 8. Said filter unit is preferably a Micron-10® filter unit.

This invention also provides a reversible-well collection plate comprising polypropylene and Teflon® and containing 96 wells, wherein: each of said wells is capable of securely containing a Microcon-3, 10, 30 or 100® filter unit; the top of said well is capable of securely containing either end of the filter unit; wherein the wells have a U-shaped bottom surface sufficient to allow said surface to securely contain either end of said filter unit; and wherein: the side and bottom surfaces of said filtrate collection plate contain a plurality of V-shaped grooves sufficient in number and size to allow the plate by a standard automated device; and, the external dimensions of said filtrate collection plate are about the same as the external dimensions of a standard 96-well plate. Preferably, the plate is composed of from about 1–10% Teflon® and from about 80–99% polypropylene, most preferably, about 2.5% Teflon® and about 97.5% polypropylene. Preferably, the filter unit is a Micron-10® filter unit. Said reversible-well collection plate comprising polypropylene and Teflon® and containing 96 wells substantially as shown in FIGS. 9, 10, 11 and 12.

The filtrate-holder and reversible-well collection plates are designed to work, in connection with filter units, together in high-throughput screening assays for separating out small molecules ("small" generally meaning molecules having a molecular weight of about 300–600 daltons, although smaller and larger molecules may be separated as well) which bind to certain proteins from those which don't. Thus, this invention further provides a high-throughput screening assay for the detection of the binding of small molecules to protein which comprises the steps of:

(a) loading a sample of liquid containing the small molecule into a Microcon-3, 10, 30 or 100® filter unit having a membrane to which protein is bound;

(b) placing said loaded filter unit of step (a) securely into the filtrate collection plate of claim 1;

(c) securely attaching the bottom of said loaded filtrate-holder plate of step (b) to the top of the reversible-well collection plate of claim 6, such that the base of said filter unit protrudes through the bottom of the filtrate-holder plate and fits securely into the wells of the reversible-well collection plate;

(d) collecting the filtrate from the wells of the collection plate so as to determine the small molecules which do not bind ("free") to the protein, wherein said collection is by centrifuging the plate combination of step (c) for a period of time sufficient to allow the free small molecules to pass through the filter membrane and into the collection wells, while not allowing substantially any of the bound small molecules to pass through the membrane; and, (e) collecting the bound molecules from step (d), wherein said collecting is by connecting the wells of a second reversible-well collection plate, said wells facing down, securely to the top ends of the filter units, securely inverting the filter unit/reversible-well combination and then centrifuging the inverted combination for a period of time sufficient to allow the bound small molecules to pass into the wells of the collection plate.

Said assay is readily conducted by ordinarily skilled artisans given the teachings of this invention and without undue experimentation. For example, said artisans are well able to determine sufficient centrifuging speeds and time for both the filtrate collection (e.g., 3000 rpm for 30 minutes) and retentate collection (e.g., five minutes) steps. Said assay offers a number of advantages not presently available in the high-throughput screening art. For example, due to the incorporation of Teflon® into both plates, small molecules are inhibited from sticking to the surfaces of the plates' wells, thus leading to more accurate assessments of free and bound molecules. Also, due to the nature of the structure of the wells of the reversible-well plates, having the capacity to attach to either end of the filter units, filtrate can be collected from the initial filter units in a convenient step.

The following examples further illustrate the nature of this invention. However, those of ordinary skill in the art will readily understand that these examples are merely illustrative of the invention as fully defined in the claims which follow thereafter.

EXAMPLES

Study 1
Use of Microcon-10 Filter Units Instead of Dialysis Tubing

The Microcon-10 filter units were purchased from Millipore Corporation (Danvers, Mass. catalogue #42407). The Microcon-10 filter device contains a low binding, anisotropic, hydrophilic-regenerated cellulose membrane (YM membrane) with a size exclusion of 10,000 daltons (FIG. 1). The sample reservoir containing the membrane was inserted into a microfuge tube. The sample reservoir will hold up 500 ul of solution. The liquid was passed through the size-exclusion membrane via centrifugation in a tabletop, micro-centrifuge.

Figure 2:
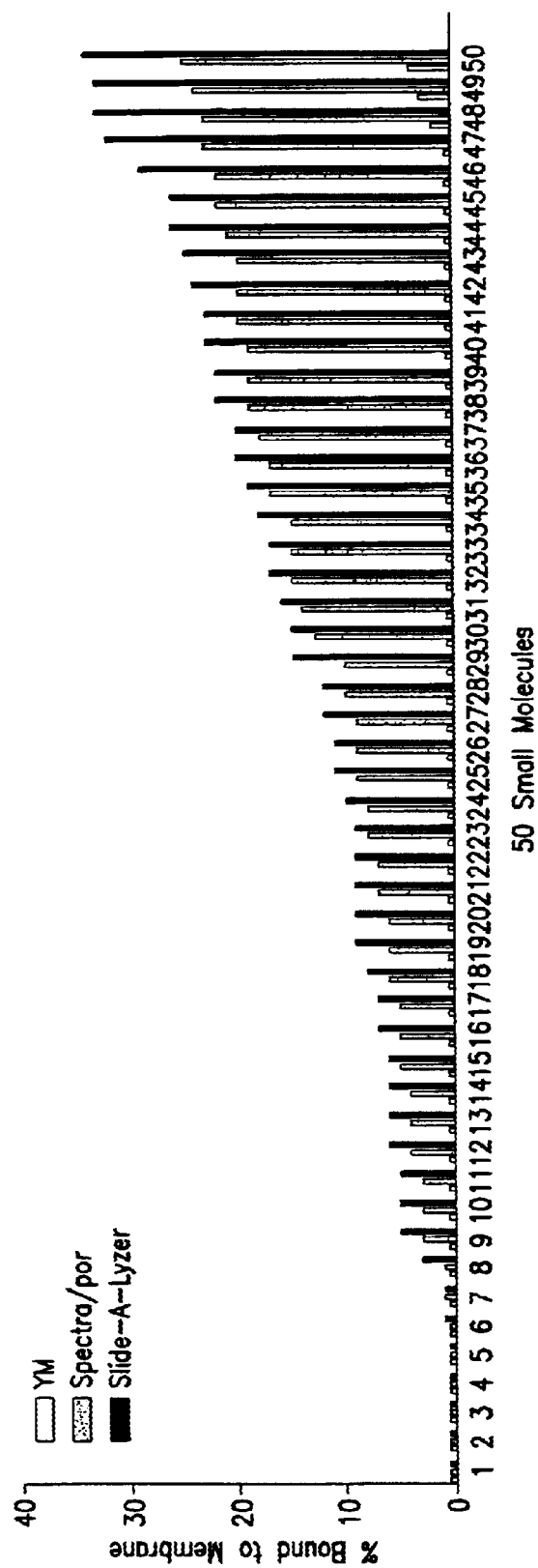
FIG. 2—Binding of Small Molecules to Membranes. The binding of 50 small molecules to the YM, Spectra/por, and Slide-A-Lyzer membranes was determined by incubating each molecule at a range of concentrations, 1–1000 nM, with each of the three membranes. The drug was allowed to incubate with the membrane in a volume of 500·1 for 30 minutes at 37° C. Following the incubation the samples were collected and the drug concentrations were calculated. The decrease in concentration was used to calculate the levels of binding to membrane.

The aim of the first experiment was to demonstrate that the YM membrane shows very low levels of binding to small molecules; if a membrane is shown to bind to a large number of different small molecules, the use of that membrane for determining an accurate protein binding value for a molecule is not possible. Binding properties of the YM membrane with that of two commercially available dialysis membranes, Spectra/Por (Spectrum, Laguna Hills, Calif. catlogue #132670) and Slide-A-Lyzer (Pierce, Rockford, Ill. catalogue #66426) were compared; both dialysis membranes contained a molecular weight cut-off of 10,000 daltons. Fifty small molecules, representing a series of hydroxamic acids, were tested for their ability to bind to the three different membranes. This was done by adding each molecule, ranging in concentration from 1–1000 nM, in a volume of 500 ul to each of the three membranes. The drugs were allowed to incubate in the membranes for 30 minutes at 37° C. Following the incubation, the amount of binding of the molecules to each membrane was calculated. This was done by removing the samples from the membranes and calculating the concentration of drug remaining by mass spectrometry or bio-assay (FIG. 2). The binding of molecules to the YM membrane was very low. Forty seven of the 50 molecules tested showed no detectable levels of binding, and three of the molecules showed 2, 3 and 4% binding, respectively. In contrast, the two other dialysis membranes showed very high binding—25 molecules showed greater than 10% binding to the Slide-A-Lyzer, with molecules 44 to 50 exhibiting greater than 25% binding. Similarly, the Spectra/Por membrane also showed very high binding—with 20 molecules exhibiting greater than 10% binding and molecules 44 to 50 showing greater than 20% binding.

Because of the high degree of binding exhibited by the Slide-A-Lyzer and Spectra/Por, the use of these membranes in a protein binding assay is unwise. For, example, determining accurate protein binding values for compounds 44–50 would be impossible using the Slide-A-Lyzer and Spectra/Por membranes. It would be very difficult to discern between how much of the molecule is bound to protein versus the membrane. In contrast, due to the low levels of binding to the YM membrane, using the Microcon-10 filter unit in a protein-binding assay would yield more accurate data.

The aim of the next experiment was to determine whether or not we could use the Microcon-10 filter units in an assay to calculate accurate protein binding values of small molecules. Also, to determine if the protein binding values generated using the Microcon-10 filter units is comparable to those values generated using the standard equilibrium dialysis method. In order to address the questions, 50 small molecules, ranging in molecular weight from 200 to 400 daltons were analyzed in parallel for binding to human serum proteins using the Microcon-10 filter units or equilibrium dialysis with the Spectra/por membranes. For the assay employing the Microcon-10 filter units, each of the 50 molecules were diluted to a final concentration of 1 uM into 500 ul of whole human serum. The samples were allowed to incubate for 30 minutes at 37° C. in an incubator. Following the incubation the samples were transferred to the Microcon-10 sample reservoirs and the free drug was separated from serum bound drug by spinning the filter units at 12,000 g at 37° C. for 10 minutes.

Twenty percent of the total volume (100 ul) was allowed to pass through and the drug concentration in the filtrate which contains the free, unbound molecule was calculated. The decrease in drug concentration in the filtrate is a measure of protein binding and is calculated by simply dividing the starting concentration [1 uM] by the concentration of drug in the filtrate. For the assay using equilibrium dialysis, each of the 50 molecules were diluted to a final concentration of 1 uM into 500 of whole human serum. The samples were allowed to incubate for 30 minutes at 37° C. in an incubator. Following the incubation, the samples were transferred to dialysis tubing with a surface area of 3 $cm^2$ and sealed with dialysis clamps. The tubing was placed in 4 liters of water that was pre-equilibrated to 37° C. Each 4-liter beaker contained 10 dialysis bags, and the samples were allowed to dialyze for 24 hours. Following the incubation, the samples were collected and the concentration of drug remaining in the bag was calculated.

Figure 3:
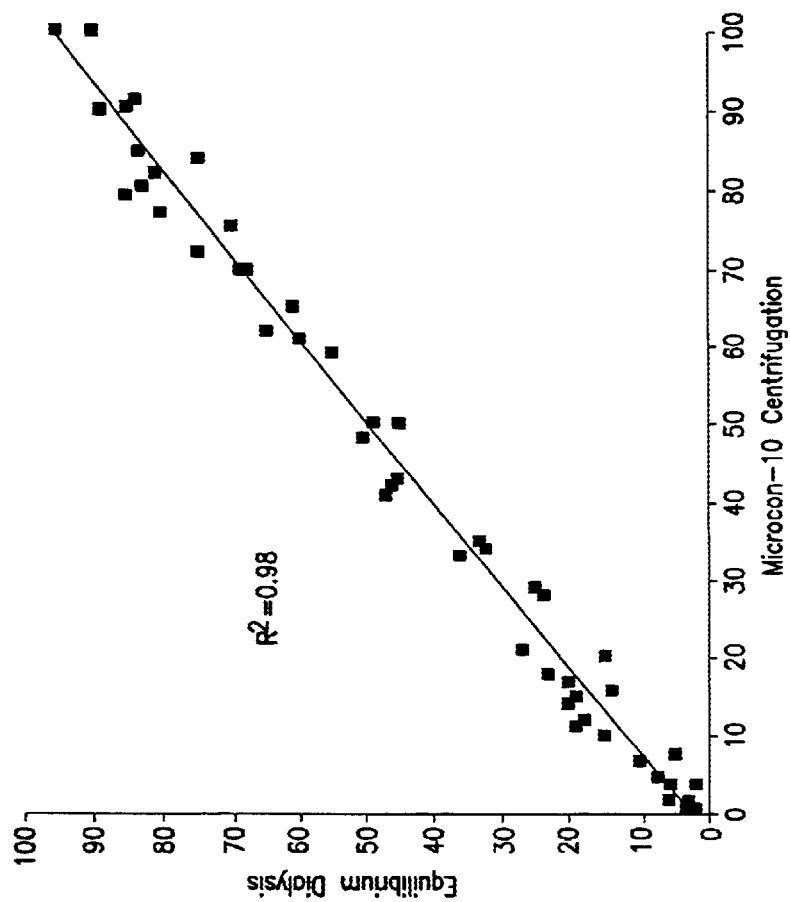
FIG. 3—Correlation Between Equilibrium Dialysis and Microcon-10 Centrifugation. The amount of serum binding of 50 small molecules were calculated using standard equilibrium dialysis and Microcon-10 centrifugation. The binding values generated in the two assays were compared and a correlation curve plotted. The $R^2$ value is 0.98.

The decrease in drug concentration is measure of protein binding and is calculated by simply dividing the starting concentration [1 uM] by the concentration of drug remaining following dialysis. The protein binding values generated in both assays were compared (see FIG. 3). There is a strong positive correlation between the binding values generated using equilibrium dialysis and Microcon-10 centrifugation. The R value is 0.98 for the 50 small molecules analyzed in the study. These data suggest that the Microcon-10 filter units can be used to calculate accurate protein binding values for small molecules comparable to equilibrium dialysis. However, there are also practical advantages in using the Microcon-10 devices for determining the protein binding of small molecules; these include speed of the assay and reduced set-up time.

Study 2
Design of Novel 96-Well Plate Device for Holding 96 Microcon-10 Filter Units and Capable of Collecting the Filtrate and Retentate The development of a 96-well plate device to accommodate 96 filter units would greatly increase the screening capacity and allow the simultaneous analysis of several hundred compounds in one assay. Two such devices are described herein, a filtrate plate device (see U.S. Provisional Application Ser. No. 60/127,624) and a reversible-well plate device (U.S. Provisional Application Serial No. 60/145, 527). Each plate holds 96 Microcon-10 filter units and possesses the external dimensions of a standard 96-well plate.

Figure 4:
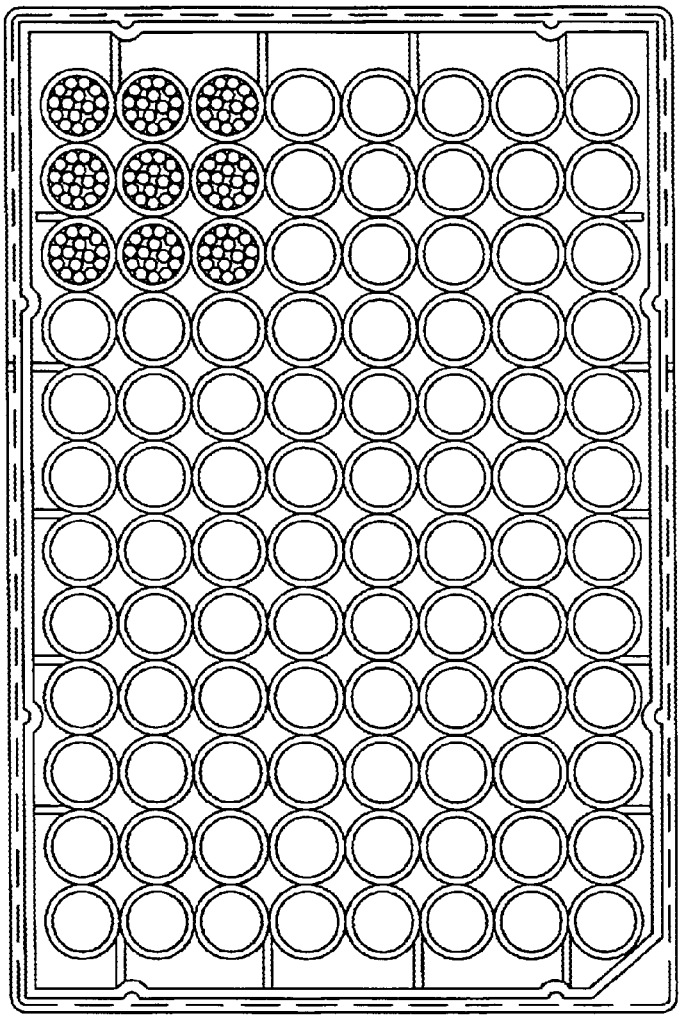
FIG. 4—Filtrate Holder. Top view of the filtrate-holder containing a novel micro-array format which allows it to hold 96 Microcon filter units. The holder contains 96 through holes where the base of the filter unit passes through and protrudes into the reversible-well collection plate.
Figure 6:
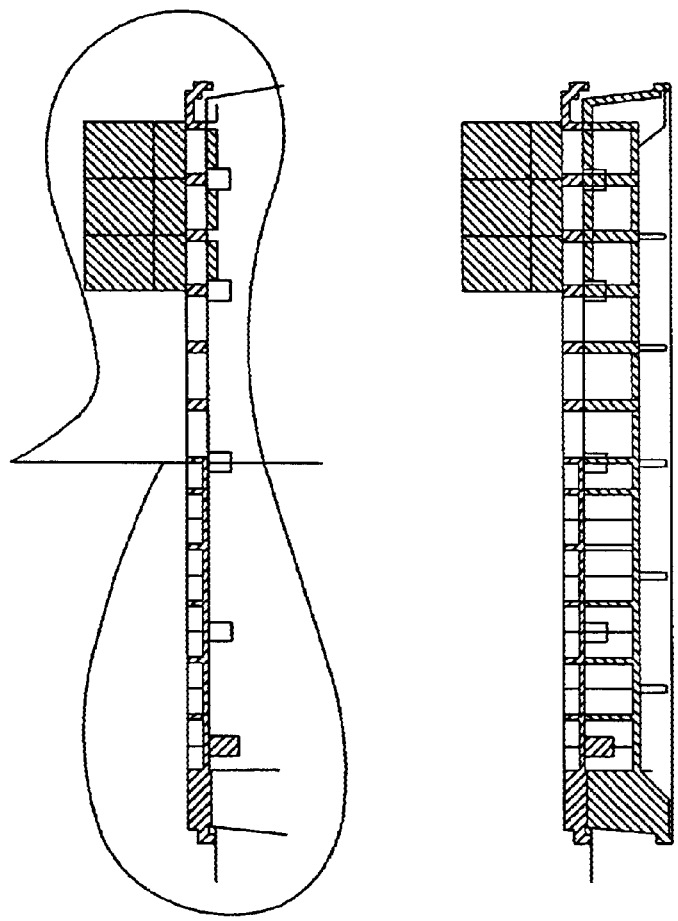
FIG. 6—Filtrate Holder. Illustrates assembly of the filtrate holder and collection plate. The holder containing 96 Microcon units is placed on top of the collection plate. The base of the filter units protrude into the wells and the pegs on the bottom of the holder seal the two parts.
Figure 10:
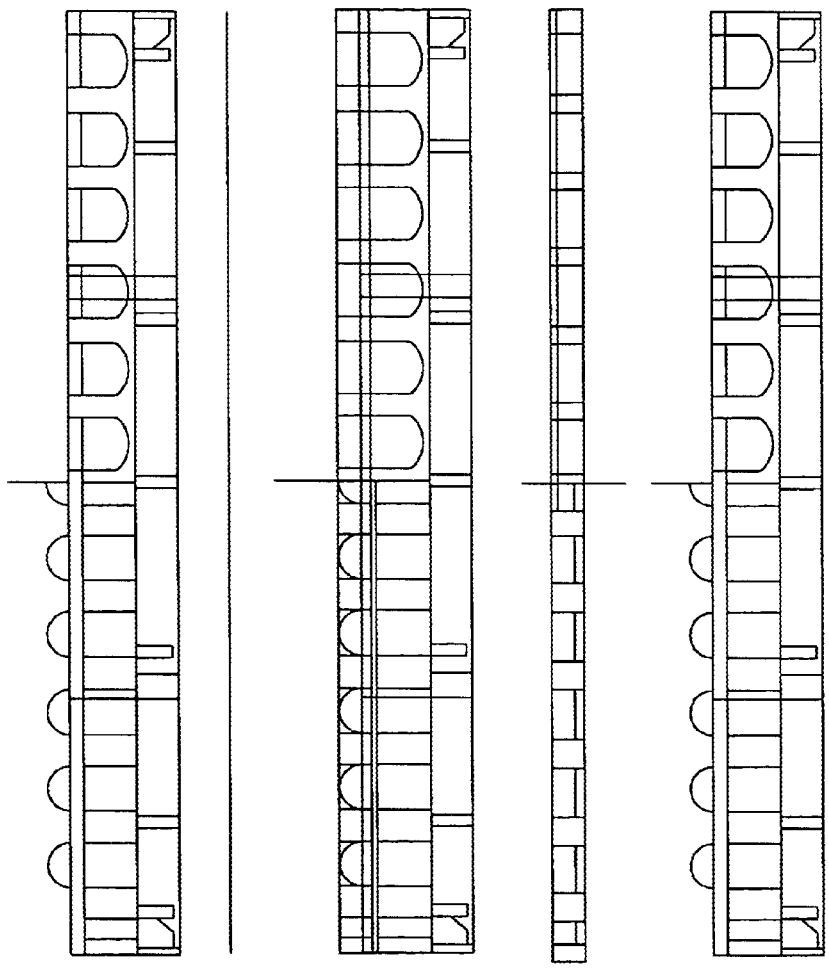
FIG. 10—Reversible-Well Holder. The diagram is a side view of the alignment of retentate holder and collection plate. The diagram illustrates that the micro-array format between the holder and collection plate are in alignment.

The filtrate plate device (Tf) consists of a 96-well plate and holder with a unique micro-array format designed to fit 96 Microcon filter units. The holder contains 96 through-holes where the filter units are inserted (FIGS. 4, 5, 6). The ridge of the filter unit lies on top of the through-hole and the bottom (base) of the filter unit passes through. Once the filter units are inserted into the holder, it is placed on top of a 96-well collection plate with the same micro-array format as the holder (FIGS. 7, 8). The set-up was designed so that several mm of the base of the filter unit protrudes into the wells of the collection plate. This prevents well to well spill-over during the centrifugation. The holder/plate sandwich can be spun in a tabletop centrifuge with a swinging bucket to collect the filtrate. The Tf-plates were designed to allow stacking of the sandwiches on top of one another to allow more plates to be spun at one time.

Example protocol: Microcon-10 units are inserted into the custom-designed holder which is then placed on top of the collection plate. 200 ul human serum is added to the filter units in the presence or absence of the small molecule at a concentration of 1 uM. The plates are placed in a swinging bucket rotor, containing microtiter plate holders. The plates are spun at 3000 g for 30 minutes. The free small molecules (typical molecular weight 300–600 Daltons) readily pass through the filter membrane and pass into the collection well. The bound molecules are retained with the plasma proteins, which range in molecular weight from 20,000 to 500,000 Daltons. The collection plate contains the free compound (filtrate) and the filter reservoir contains the bound compound (retentate). The free compound contained in the filtrate can be determined by mass spectrophotometry, electrospay or a bioassay.

In order to collect to retentate, another collection plate was placed with the wells facing down on top of filter units. The plate was designed to fit tightly around the open end of the filter units. Next, the holder was inverted and spun an additional five minutes to collect the retentate into the second collection plate. The filtrate is then ready to be analyzed for bound compound. Finally, the -filtrate and reversible well plates are designed with V-grooves on the outer exterior of the plates that make them amenable to automation using robotics.

Study 3
Formulation of Plasticware Capable of Reducing the Binding of Small Molecules to the Bottom of the Wells in the Collection Plates.

Both the Tr and Tf collection plates were originally composed of pure polypropylene. However, following a protein-binding assay, the free drug contained in the filtrate showed binding to the bottom of the well. This binding to polypropylene was seen for many small molecules. Therefore, in many cases the calculated concentration of drug in the filtrate was incorrect and lead to the extrapolation of erroneous protein binding values. In order to eliminate the binding of small molecules to the polypropylene plates a novel mixture of plastic was formulated. Liquid Teflon was mixed with pure polypropylene and used to make the Tr and Tf plates. The hybrid plastic contained 2.5% Teflon and 97.5% polypropylene. In order to compare the binding properties of the hybrid plastic to that of pure polypropylene, the binding of 50 small molecules to both plastics were determined. This was done by incubating each of the small molecules at a range of concentrations (1–1000 nM) in the well of a plate composed of pure polypropylene or polypropylene with 2.5% Teflon. The small molecules were allowed to incubate in the well in a volume of 200·1 of water for 30 minutes at 37° C.

Following the incubation the samples were removed from the wells and the concentration of drug was calculated using mass spectrometry or bio-assay. The incorporation of the. Teflon eliminated binding to the bottom of the wells almost completely (FIG. 13). These data suggest that the incorporation of Teflon into polypropylene plates will be very valuable in reducing binding of small molecules and peptides to the bottom of the wells. This is the first demonstration of a 96-well plate composed of polypropylene and Teflon®.

What is claimed is:

1. A filtrate-holder plate comprising polypropylene and polytetrafluoroethylene resin and containing a plurality of wells, wherein:

each of said wells is capable of securely containing a centrifugal filter unit having a base, reservoir and filter membrane;

said wells contain an opening on their bottom surface sufficient in size to allow said base of said filter unit, but not said reservoir or filter membrane of said filter unit, to pass through said bottom surface and into a reversible-well collection plate;

said wells having a circular circumference;

and wherein:

said filtrate-holder plate has side surfaces and an exterior bottom surface that contains a plurality of pegs protruding therefrom sufficient in number and size to connect said plate to a reversible-well collection plate; and said side and bottom surfaces of said filtrate-holder plate contain a plurality of V-shaped grooves sufficient in number and size to allow said filtrate-holder plate to be held by a standard automated device.

2. The plate of claim 1, wherein said filtrate-holder plate is composed of from about 1–10% polytetrafluoroethylene resin and from about 80–99% polypropylene.

3. The plate of claim 2, wherein said filtrate-holder plate is composed of from about 2.5% polytetrafluoroethylene resin and from about 97.5% polypropylene.

4. The filtrate holder of claim 1, wherein said membrane in said filter unit has a nominal molecular weight limit cut-off of 10,000.

5. The filter-holder plate of claim 1, wherein there are 96 wells.

6. In combination, a filtrate-holder plate and a plurality of filter units, wherein:
   said filter-holder plate comprises a substrate having a top surface, a bottom surface and a thickness, said substrate having a plurality of holes in said thickness arranged in an array;
   each of said plurality of filter units comprises a base having a perimeter, a reservoir and a membrane between said base and said reservoir, the length of said base being greater than said thickness of said substrate;
   each of said plurality of holes is configured to receive said base of a respective one of said plurality of filter units such that said base extends through said hole and beyond said bottom surface of said substrate; and
   said substrate comprises a blend of polytetrafluoroethylene resin and polypropylene.

7. The combination of claim 6, wherein said blend comprises from about 1–10% polytetrafluoroethylene and from about 80–99% polypropylene.

8. The combination of claim 6, wherein said blend comprises about 2.5% polytetrafluoroethylene.

9. The combination of claim 6, wherein said substrate comprises 96 holes.

* * * * *